US009702871B1

(12) United States Patent
Koh et al.

(10) Patent No.: US 9,702,871 B1
(45) Date of Patent: Jul. 11, 2017

(54) SYSTEM AND METHOD FOR DETECTING COMPONENTS OF A MIXTURE INCLUDING A VALVING SCHEME FOR COMPETITION ASSAYS

(71) Applicant: National Technology & Engineering Solutions of Sandia, LLC, Albuquerque, NM (US)

(72) Inventors: Chung-Yan Koh, Dublin, CA (US); Matthew E. Piccini, Belmont, CA (US); Anup K. Singh, Danville, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 78 days.

(21) Appl. No.: 14/546,876

(22) Filed: Nov. 18, 2014

(51) Int. Cl.
*B01L 3/00* (2006.01)
*G01N 33/543* (2006.01)

(52) U.S. Cl.
CPC .... *G01N 33/54306* (2013.01); *B01L 3/50273* (2013.01); *B01L 3/502738* (2013.01); *B01L 3/502761* (2013.01); *G01N 33/54366* (2013.01); *B01L 2200/0652* (2013.01); *B01L 2300/069* (2013.01); *B01L 2300/0672* (2013.01); *B01L 2300/0803* (2013.01); *B01L 2300/087* (2013.01); *B01L 2400/0409* (2013.01); *B01L 2400/0683* (2013.01)

(58) Field of Classification Search
None
See application file for complete search history.

(56) References Cited

U.S. PATENT DOCUMENTS

| | | |
|---|---|---|
| 3,555,284 A | 1/1971 | Anderson |
| 3,744,974 A | 7/1973 | Maddox et al. |
| 4,125,375 A | 11/1978 | Hunter |
| 4,156,570 A | 5/1979 | Wardlaw |
| 4,554,071 A | 11/1985 | Ruijten et al. |
| 4,656,143 A | 4/1987 | Baker et al. |

(Continued)

FOREIGN PATENT DOCUMENTS

| | | |
|---|---|---|
| WO | WO-2008/143578 | 11/2008 |
| WO | WO-2009/098237 | 8/2009 |

OTHER PUBLICATIONS

McBain et al., Polyethyleneimine functionalized iron oxide nanoparticles as agents for DNA delivery and transfection, Journal of Materials Chemistry, 17, pp. 2561-2565, available online Apr. 13, 2007.

(Continued)

*Primary Examiner* — Rebecca Martinez
(74) *Attorney, Agent, or Firm* — Helen S. Baca

(57) ABSTRACT

Examples are described including measurement systems for conducting competition assays. A first chamber of an assay device may be loaded with a sample containing a target antigen. The target antigen in the sample may be allowed to bind to antibody-coated beads in the first chamber. A control layer separating the first chamber from a second chamber may then be opened to allow a labeling agent loaded in a first portion of the second chamber to bind to any unoccupied sites on the antibodies. A centrifugal force may then be applied to transport the beads through a density media to a detection region for measurement by a detection unit.

34 Claims, 10 Drawing Sheets

(56) References Cited

U.S. PATENT DOCUMENTS

| | | | |
|---|---|---|---|
| 4,683,579 | A | 7/1987 | Wardlaw |
| 4,844,818 | A | 7/1989 | Smith |
| 5,279,936 | A | 1/1994 | Vorpahl |
| 5,635,362 | A | 6/1997 | Levine et al. |
| 5,705,628 | A | 1/1998 | Hawkins |
| 5,882,903 | A | 3/1999 | Andrevski et al. |
| 6,153,148 | A | 11/2000 | Thomas |
| 6,319,469 | B1 | 11/2001 | Mian et al. |
| 6,503,722 | B1 | 1/2003 | Valkirs |
| 6,887,384 | B1 | 5/2005 | Frechet et al. |
| 6,960,449 | B2 | 11/2005 | Wang et al. |
| 7,033,747 | B2 | 4/2006 | Gordon et al. |
| 7,157,049 | B2 | 1/2007 | Valencia et al. |
| 7,312,085 | B2 | 12/2007 | Chou et al. |
| 7,332,326 | B1 | 2/2008 | Kellogg et al. |
| 7,758,810 | B2 | 7/2010 | Lee et al. |
| 8,337,775 | B2 | 12/2012 | Pugia et al. |
| 8,945,914 | B1 | 2/2015 | Schaff et al. |
| 8,962,346 | B2 | 2/2015 | Schaff et al. |
| 9,186,668 | B1 | 11/2015 | Schaff et al. |
| 9,244,065 | B1 | 1/2016 | Schaff et al. |
| 9,304,128 | B1 | 4/2016 | Koh et al. |
| 9,304,129 | B2 | 4/2016 | Schaff et al. |
| 2001/0055812 | A1 | 12/2001 | Mian et al. |
| 2002/0098535 | A1 | 7/2002 | Wang et al. |
| 2002/0106786 | A1* | 8/2002 | Carvalho ............ B01F 5/0647 435/287.3 |
| 2002/0137068 | A1 | 9/2002 | Haugland et al. |
| 2002/0151043 | A1 | 10/2002 | Gordon |
| 2002/0153251 | A1 | 10/2002 | Sassi et al. |
| 2002/0164659 | A1 | 11/2002 | Rao et al. |
| 2002/0170825 | A1 | 11/2002 | Lee et al. |
| 2003/0013203 | A1 | 1/2003 | Jedrzejewski et al. |
| 2003/0124719 | A1 | 7/2003 | Woodside |
| 2003/0203504 | A1 | 10/2003 | Hefti |
| 2004/0072278 | A1 | 4/2004 | Chou et al. |
| 2005/0186685 | A1 | 8/2005 | Kange et al. |
| 2005/0215410 | A1 | 9/2005 | Merino et al. |
| 2005/0282220 | A1 | 12/2005 | Prober et al. |
| 2006/0171654 | A1 | 8/2006 | Hawkins et al. |
| 2008/0108047 | A1 | 5/2008 | Woodside |
| 2008/0149484 | A1 | 6/2008 | Tolley et al. |
| 2009/0004059 | A1 | 1/2009 | Pugia et al. |
| 2009/0069554 | A1 | 3/2009 | Finne |
| 2009/0209402 | A1 | 8/2009 | Andersson |
| 2009/0325186 | A1 | 12/2009 | Hinnah et al. |
| 2010/0068754 | A1 | 3/2010 | Kirakossian |
| 2010/0120596 | A1 | 5/2010 | Froman et al. |
| 2010/0151560 | A1 | 6/2010 | Wo et al. |
| 2011/0045958 | A1 | 2/2011 | Pedrazzini |
| 2014/0273241 | A1 | 9/2014 | Ochranek et al. |
| 2015/0360225 | A1 | 12/2015 | Schaff et al. |
| 2016/0061829 | A1 | 3/2016 | Schaff et al. |
| 2016/0178619 | A1 | 6/2016 | Koh et al. |

OTHER PUBLICATIONS

Abi-Samra, Kameel et al., "Infrared controlled waxes for liquid handling and storage on a CD-microfluidic platform", The Royal Society of Chemistry; Lab on a Chip, 2011, 723-726.

Ahanotu, et al., "Staphylococcal enterotoxin B as a Biological Weapon: Recognition, Management, and Surveillance of Staphylococcal enterotoxin", Applied Biosafety; vol. 11 (3), 2006, 120-126.

Albrecht, J.W. et al., "Micro Free-Flow IEF Enhanced Active Cooling and Functionalized Gels", Electrophoresis, 2006, pp. 4960-4969, vol. 27.

Amersham, , "Percoll: Methodology and Applications", 2001, 1-84.

Amukele, et al., "Ricin A-chain activity on stem-loop and unstructured DNA substrates.", Biochemistry; vol. 44(11), Mar. 25, 2005, 4416-4425.

Andersson, et al., "Parallel nanoliter microfluidic analysis systems", Clinical Chemistry, 2007.

Balwin, Robert L. , "How Hofmeister Ion Interactions Affect Protein Stability", Biophysical Journal; vol. 71, Oct. 1996, 2056-2063.

Berry, Scott M., "One-step Purification of Nucleic Acid for Gene Expression Analysis via Immiscible Filtration Assisted by Surface Tension", Lab Chip, May 21, 2011.

Boyko, Matthew et al., "Cell-Free DNA—a Marker to Predict Ischemic Brain Damage in a Rat Stroke Experimental Model", Journal of Neurosurg Anesthesiol, vol. 23, No. 3, Jul. 2011, 222-228.

Brigotti, et al., "Shiga toxin 1 acting on DNA in vitro is a heat-stable enzyme not requiring proteolytic activation", Biochimie Journal; 86(45), 2004, 305-309.

Carney, J. , "Rapid Diagnostic Tests Employing Latex Particles", Analytical Proceedings, Apr. 1990, 99-100.

Curtis, R. A. et al., "A Molecular approach to bioseparations: Protein-protein and protein-salt interactions", Chemical Engineering Science; vol. 61, 2006, 907-923.

Czeiger, David et al., "Measurement of Circulating Cell-Free DNA Levels by a New Simple Fluorescent Test in Patients With Primary Colorectal Cancer", Am J Clin Pathol, 2011, 264-270.

Endo, et al., "RNA N-Glycosidase Activity of Ricin A-Chain. Mechanism of Action of the Toxin Lectin Ricin on Eukaryotic Robosomes", The Journal of Biological Chemistry, vol. 262, No. 17, Jun. 15, 1987, 8128-8130.

Glorikian, Harry et al., "Smart-consumables product development: Implications for molecular diagnostics", DX Direction, 2010, 12-16.

Glorikian, H. et al., "Overview of Microfluidic Applications in IVDS", DX Direction 1, pp. 12-16 (2010).

Goldshtein, Hagit et al., "A Rapid Direct Fluorescent Assay for Cell-Free DNA Quantification in Biological Fluids", Annals of Clinical Biochemistry, 2009, 488-494.

Gorkin, et al., "Centrifugal microfluidics for biomedical applications", www.rsc.org/loc; Lab on a Chip, May 2010, 1758-1773.

Holmberg, et al., "Depurination of A4256 in 28 S rRNA by the Ribosome-inactivating Proteins from Barley and Ricin Results in Different Ribosome Conformations", Journal of Molecular Biology; vol. 259(1), May 31, 1996, 81-94.

Holmes, David et al., "Leukocyte analysis and differentiation using high speed microfluidic single cell impedance cytometry", Lab on a Chip 9, Aug. 7, 2009, 2881-2889.

Huang, et al., "The Primary Structure of Staphylococcal enterotoxin B. III. The Cyanogen Bromide Peptides of Reduced and Aminoethylated enterotoxin B, and the Complete Amino Acid Sequence.", The Journal of Biological Chemistry vol. 245 No. 14, Jul. 25, 1970, 3518-3525.

International Search Report and Written Opinion dated Jun. 28, 2013 for PCT/US2013/032349.

Lee, et al., "Fully integrated lab-on-a-disc for simultaneous analysis of biochemistry and immunoassay from whole blood", Lab Chip, 2011.

Lee, B. S. et al., "A fully automated immunoassay from whole blood on a disc", Lab on a Chip 9, Mar. 5, 2009, 1548-1555.

Lim, C. T. et al., "Bead-based microfluidic immunoassays: The next generation", Biosensors Bioelectronics 22, Jul. 20, 2006, 1197-1204.

Lo, C.T. et al., "Photopolymerized Diffusion-Defined Polyacrylamide Gradient Gels for On-Chip Protein Sizing", The Royal Society of Chemistry, Lab on a Chip, vol. 8, No. 8, 2008, pp. 1273-1279.

Lo, Y. M. D. et al., "Plasma DNA as a Prognostic Marker in Trauma Patients", Clinical Chemistry 46:3, 2000, 319-323.

Madou, Marc et al., "Lab on a CD", Annual Rev. Biomed Eng 8, May 2006, 601-628.

Maes, Melissa L. et al., "Comparison of Sample Fixation and the use of LDS-751 or anti-CD45 or Leukocyte Identification in Mouse Whole Blood for Flow Cytometry", Journal of Immunological Methods, 319(1-2) Jan. 30, 2007, 79-86.

Min, Junhong et al., "Functional Integration of DNA Purification and Concentration Into a Real Time Micro-PCR Chip", The Royal Society of Chemistry; Lab on a Chip, 2011, 259-265.

(56) References Cited

OTHER PUBLICATIONS

Price, Christopher P. et al., "Light-Scattering Immunoassay", Principles and Practice of Immunoassay (Second Edition); Chapter 18, 1997, 445-480.
Rhodes, Andrew et al., "Plasma DNA concentration as a predictor of mortality and sepsis in critically ill patients", Critical Care, 2006, 1-7.
Rider, Todd H. et al., "A B Cell-Based Sensor for Rapid Identification of Pathogens", www.sciencemag.org; Science vol. 301, Jul. 11, 2003, 213-215.
Riegger, L. et al., "Read-out concepts for multiplexed bead-based fluorescence immunoassays on centrifugal microfluidic platforms", Sensors and Actuators A-Physical, 2006, 455-462.
Saukkonen, et al., "Cell-Free Plasma DNA as a Predictor of Outcome in Severe Sepsis and Septic Shock", Clinical Chemistry; vol. 54:6, 2008, 1000-1007.
Schaff, et al., "Whole Blood Immunoassay Based on Centrifugal Bead Sedimentation", Clinical Chemistry Automation and Analytical Techniques 57:5, 2011, 753-761.
Schembri, et al., "Portable Simultaneous Multiple Analyte Whole-Blood Analyzer for Point-of-Care Testing", Clinical Chemistry 38/9, 1992, 1665-1670.
Schneider, et al., "Characterization of EBV-Genome Negative "Null" and "T" Cell Lines Derived From Children With Acute Lymphoblastic Leukemia and Leukemic Transformed Non-Hodgkin Lymphoma", International Journal of Cancer; 19(5), May 15, 1977, 621-626.
Yu, et al., "Bioinformatic processing to identify single nucleotide polymorphism that potentially affect Ape1 function.", Mutation Research/Genetic Toxicology and Environmental Mutagenesis; vol. 722(2), Jun. 17, 2011, 140-146.
Zhang, L. et al., "A New Biodosmetric Method: Branched DNA-Based Quantative Detection of B1 DNA in Mouse Plasma", The British Journal of Radiology, vol. 83, Aug. 2010, 694-701.
Ziegler, Annemarie et al., "Circulating DNA: a new diagnostic gold mine?", Cancer Treatment Reviews, vol. 28, 2002, 255-271.
Riahi et al. Analytical Chemistry. 2011. 83(16): 6349-6354 and Supporting Information.
Melting Temperature Calculation. Retrieved on asf from the internet: http://www.biophp.org/minitools/melting_temperature/demo.php?primer=CGT+TAC+CCG+CAG&basic-1&NearestNeighbor=1&cp=200&cs=50&cmg=0.
Berlier et al. The Journal of Histochemistry and Cytochemistry. 2003. 51(12): 1699-1712.
Churchill et al., "Detection of Listeria monocytogenes and the toxin listeriolysin O in food", Journal of Microbiological Methods, 2006; 64:141-170.
U.S. Appl. No. 13/423,008, filed Mar. 16, 2012, Schaff et al.
U.S. Appl. No. 13/941,186, filed Jul. 12, 2013, Koh et al.
U.S. Appl. No. 14/957,405, filed Dec. 2, 2015, Koh et al.
U.S. Appl. No. 14/090,040, filed Nov. 26, 2013, Koh et al.
U.S. Appl. No. 14/256,294, filed Apr. 18, 2014, Sommer et al.
Carbera CR et al., "Formation of natural pH gradients in a microfluidic device under flow conditions: model and experimental validation," Anal. Chem. 2001;73(3):658-66.
Cui H et al., "Multistage isoelectric focusing in a polymeric microfluidic chip," Anal. Chem. 2005;77(24):7878-86.
Das C et al., "Effects of separation length and voltage on isoelectric focusing in a plastic microfluidic device," Electrophoresis 2006;27(18):3619-26.
Fologea D et al, "Detecting single stranded DNA with a solid state nanopore," Nano Lett. 2005;5(10):1905-9.
IVD Technology, "Microfluidic Applications for IVDs," DX Directions 2010;Spring:1-26.
Gusev I et al., "Capillary columns with in situ formed porous monolithic packing for micro high-performance liquid chromatography and capillary electrochromatography," J. Chromatogr. A 1999;855(1):273-90.
Hatch AV et al., "Integrated preconcentration SDS-PAGE of proteins in microchips using photopatterned cross-linked polyacrylamide gels," Anal. Chem. 2006;78(14):4976-84.
Herr AE et al., "Microfluidic immunoassays as rapid saliva-based clinical diagnostics," Proc. Nat'l Acad. Sci. USA 2007;104(13):5268-73.
Herr Ae et al., "On-chip coupling of isoelectric focusing and free solution electrophoresis for multidimensional separations," Anal. Chem. 2003;75(5):1180-7.
Lim P et al., "Rapid isoelectric trapping in a micropreparative-scale multicompartment electrolyzer," Electrophoresis 2007;28(12):1851-9.
Long Z et al., "Integration of nanoporous membranes for sample filtration/preconcentration in microchip electrophoresis," Electrophoresis 2006;27(24):4927-34.
PubChem Search results for "2,3-dihydroxpropyl octanoate," retrieved on Oct. 5, 2016 from https://www.ncbi.nlm.nih.gov/pcompound/?term=2%2C3-dihydroxpropyl+octanoate (4 pp.).
PubChem Entry for "Tween 20," retrieved on Oct. 4, 2016 from https://pubchem.ncbi.nlm.nih.gov/compound/Tween_20#section=Names-and-identifiers (2 pp.).
Sigma-Aldrich product page for Tween 20, archived from Jun. 28, 2012, retrieved on Oct. 5, 2016 from https://web.archive.org/web/20120628080753/http://www.sigmaaldrich.com/catalog.product/sial/p1379?ang=en&region= (43 pp.).
Sommer GJ et al., "On-chip isoelectric focusing using photopolymerized immobilized pH gradients," Anal. Chem. 2008;80(9):3327-33.
Tan Wet al., "Miniaturized capillary isoelectric focusing in plastic microfluidic devices," Electrophoresis 2002;23(20):3638-45.
Zilberstein G et al., "Parallel isoelectric focusing chip," Proteomics 2004;4(9):2533-40.
Zilberstein GV et al., "Parallel isoelectric focusing II," Electrophoresis 2004;25(21-22):3643-51.
Zilberstein GV et al., "Parallel processing in the isoelectric focusing chip," Electrophoresis 2003;24(21):3735-44.
Zuo X et al., "A method for global analysis of complex proteomes using sample prefractionation by solution isoelectrofocusing prior to two-dimensional electrophoresis," Anal. Biochem. 2000;284(2):266-78.

* cited by examiner

SYSTEM AND METHOD FOR DETECTING COMPONENTS OF A MIXTURE INCLUDING A VALVING SCHEME FOR COMPETITION ASSAYS

STATEMENT REGARDING RESEARCH & DEVELOPMENT

This invention was developed under Contract DE-AC04-94AL85000 between Sandia Corporation and the U.S. Department of Energy. The U.S. Government has certain rights in the invention.

TECHNICAL FIELD

Embodiments of the invention relate generally to measurement systems and examples include methods, systems and apparatus including mechanisms for conducting competition assays for the detection and/or quantification of a target analyte in a sample. Examples of microfluidic disks including mechanisms for conducting competition assays are described.

BACKGROUND

Measurement of samples is important in a number of industries, such as the chemical and biotechnology industries, where the concentration of certain components of the sample is of interest. For example, quantification of biomolecules such as proteins and nucleic acids from patient samples is an important area of research and commercial development. Quantification of biomolecules and other types of samples is typically performed by optical measurements including fluorescence, luminescence, or relative light absorption. Portable solutions for these applications are a large and growing segment of the overall market. Existing portable solutions typically require specialized personnel, and may be bulky and time-consuming to operate.

Measurement systems sometimes perform sandwich ELISA assays in which two antibodies participate in the assay. This may be achieved by using a capture antibody to immobilize the antigen on a solid support and a labeled detection antibody for quantification. Sandwich ELISA assays generally may be performed in a single chamber because of the specificity of the monoclonal antibodies, which typically do not cross-react and do not bind to each other in the absence of the antigen. While sandwich ELISA assay may be sufficient for detection of some types of target analytes, competition ELISA may provide a greater sensitivity for detection of certain target analytes.

Competition ELISA generally involves antibodies immobilized on a solid support. Antigen in the sample may bind to sites on the antibodies. Following a period of time where antigen in a sample is allowed to bind, labeled antigen that is selected to bind to the same or similar sites on the antibodies is introduced. The labeled antigen "competes" for sites with the antigen in the sample. To the extent antigen was not present in the sample, sites will remain for the labeled antigen to bind. In this manner, the amount of signal in the competition assay may be inversely proportional to the quantity of antigen in the sample.

DETAILED DESCRIPTION

Figure 1:
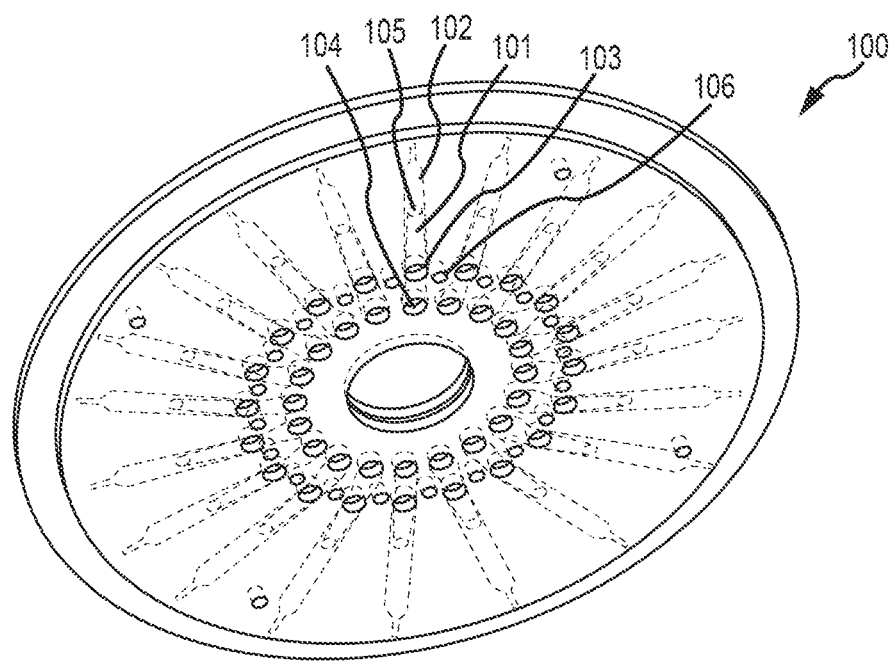
FIG. 1 is a top down schematic illustration of an assay device arranged in accordance with embodiments of the present invention.

Certain details are set forth below to provide a sufficient understanding of embodiments of the invention. However, it will be clear to one skilled in the art that embodiments of the invention may be practiced without various of these particular details. In some instances, well-known chemical structures, chemical components, molecules, materials, electronic components, circuits, control signals, timing protocols, and software operations have not been shown in detail in order to avoid unnecessarily obscuring the described embodiments of the invention.

Disclosed herein are example embodiments of systems, apparatuses and methods for detecting and/or quantifying one or more components of a sample. Examples are described include mechanisms for conducting competition assays for detection and/or quantification of a target analyte in the sample. As mentioned above, existing systems and methods for performing an assay may be cumbersome and offer limited sensitivity. Therefore, there may be a need for user friendly systems and methods to perform a competitive assay quickly, accurately, and at a relatively low cost. Disclosed systems and methods may be used to perform chemical assays, biochemical assays, protocols, sample preparation or other tasks including staged delivery and management of fluids.

A competition assay, such as enzyme multiplied immunoassay technique (EMIT) may be conducted for qualitative and quantitative analysis of components in a sample. Competition assays are generally useful for detection of small molecules such as metabolites. EMIT, for example, may be used for determination of drugs and certain proteins. In a competition assay, an unlabeled antigen and a labeling agent, for example a labeled antigen, generally compete for a limited amount of specific antibody binding sites. The unlabeled antigen may be associated with a target analyte of the sample. During a competition assay, the unlabeled antigen may be allowed to bind to an antibody. In some examples, the antibody may be associated with (e.g. bound to) beads. In some examples, the beads may be coated with the antibodies. It may be advantageous to allow the unlabeled antigen to bind with the antibody in the absence of the labeled antigen, so as to achieve substantially complete binding of the unlabeled antigen in the sample. During a competition assay, the labeled antigen may be allowed to bind to unoccupied sites on the antibodies. In some examples, the labeled antigen may be allowed to bind to substantially all the unoccupied sites on the antibodies. In some examples, the labeled antigen may compete with the target analyte for sites on the antibodies. In this manner, the amount of labeled antigen detected may be correlated to the amount of unlabeled antigen in the sample, and therefore correlated to the amount of target analyte in the sample. Thus, the amount of target analyte in the sample may be quantified by detecting the amount of labeled antigen bound to the antibodies. The amount of target analyte in the sample may be inversely proportional to the amount of labeled antigen in the sample. Thus, a strength of the signal detected may be inversely proportional to the amount of the target analyte in the sample.

FIG. 1 is a top down schematic illustration of an assay device 100, according to one embodiment. The assay device 100 may include features for conducting a competition assay, as will be described below. In some examples, the assay device 100 may be generally circular in shape. The assay device 100, including each layer of the assay device 100, may be formed by known manufacturing methods including, but not limited to, microfluidic manufacturing techniques and semiconductor manufacturing techniques. Techniques such as injection molding, cutting, or both, may be used. The assay device 100 may be disposable in some examples. The assay device 100 may be portable in some examples.

The assay device 100 may include a control region 105 in which a fluidic connection may be made between a first chamber 101 of the assay device 100 and a first portion 901 of a second chamber 102 of the assay device 100, as will be described below. The control region 105 may be an area in one or more layers of the assay device 100 in which an opening may be created. The assay device 100 may include features in the control region 105 to provide the fluidic connection. For example, pins may be placed in the control region 105, as will be described below. In other examples, wax or another sacrificial layer may be present in the control region 105 that may be melted or otherwise removed to create a fluidic connection. It may be advantageous to separate the first chamber 101 and the second chamber 102 to perform certain steps of a competitive assay, and then connect the first chamber 101 and the second chamber 102 to perform subsequent steps, as will be described below. Additionally, the assay device 100 may be manufactured so that the control region 105 in each layer facilitates opening to create the fluid connection, for example with perforations or a decreased thickness.

Figure 2:
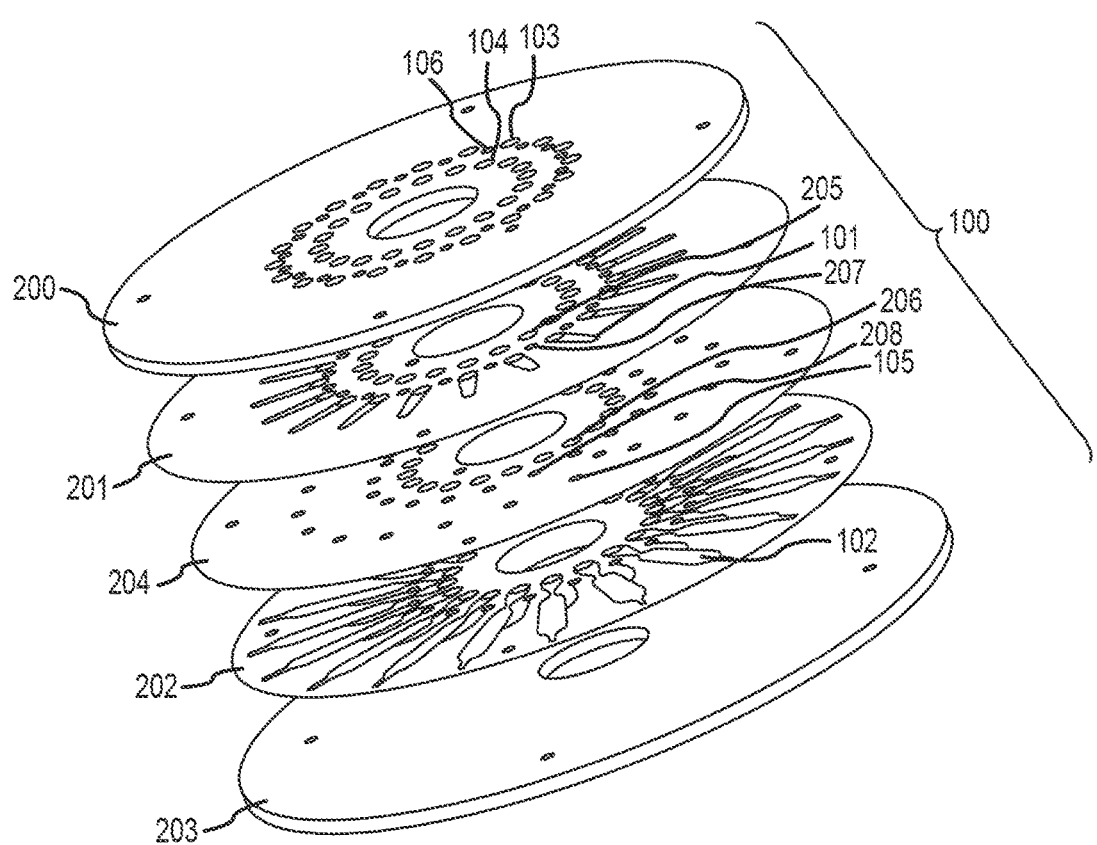
FIG. 2 is a top down exploded schematic illustration of an assay device including multiple layers, according to examples of the present invention.

FIG. 2 is a top down exploded schematic illustration of an assay device 100 including multiple layers, according to some embodiments. In some examples, the assay device may include an inlet layer 200, a first chamber layer 201, a second chamber layer 202, a bottom layer 203, and a control layer 204. It will be understood that the assay device 100 may include additional layers depending on a number of parameters of the assay, such as the number of reagents involved, likelihood of cross-reactions, etc. The additional layers may include additional chambers for loading a number of samples and/or reagents. Furthermore, additional chambers with a variety of features may be included in each layer. Embodiments disclosed herein are merely examples, and one skilled in the art will appreciate that chambers may be included in a number of arrangements depending on the assay being conducted. The inlet layer 200 may provide conduits for loading a sample and/or reagents involved with the assay. The inlet layer 200 may be a material formed by techniques such as but not limited to injection molding, cutting, deposition, etching, or combinations thereof.

The inlet layer 200 may include one or more inlets for loading of samples, reagents, or combinations thereof. The inlet layer 200 may include a first chamber inlet 103 positioned adjacent to a first chamber 101 of the assay device 100. The first chamber inlet 103 may be an opening on an inlet layer 200 (see, e.g., FIGS. 2 and 4). The first chamber inlet 103 may provide a conduit whereby a sample may be loaded into the first chamber 101. In some examples, the first chamber inlet may also be used to load other reagents, for example coated beads. In some examples, the first chamber inlet may be sealed after the samples and other reagents are loaded to prevent leakages.

The inlet layer 200 may include a second chamber inlet 104 positioned proximate to a second chamber 102 of the assay device 100. The second chamber inlet 104 may be an opening on the inlet layer 200. The second chamber inlet 104 may be a conduit that couples with one or more channels of one or more layers of the assay device 100, whereby a passageway is created such that reagents for conducting a competition assay may be loaded into the second chamber 102. As will be described below, the second chamber 102 may be loaded with a density media and/or a labeling agent.

The inlet layer 200 may include a vent 106 to maintain a relatively constant pressure while samples and/or reagents are being loaded. It may be advantageous to maintain a relatively constant pressure to prevent disturbances, such as bubbles forming, when the first chamber 101 and/or the second chamber 102 are being loaded or connected to one another. The vent 106 may be a conduit that may couple with one or more channels of one or more layers of the assay device 100, whereby a passageway is created such that pressure gradients may be reduced.

The first chamber layer 201 of the assay device 100 may include a first chamber 101, a first second chamber passage 205, and a first vent passage 207. The first chamber layer 201 may be positioned adjacent to the inlet layer 200. The first second chamber passage 205 may couple with the second chamber inlet 104 to provide a conduit for reagents to be loaded into the second chamber 102. The first vent passage 207 may couple with the vent 106 to provide a conduit for air to pass such that pressure gradients across the multiple layers of the assay device 100 may be reduced.

The first chamber 101 may be a compartment, recess, or another type of structure shaped to house a sample, beads coated with antibodies, or combinations thereof. The first chamber 101 may be coupled to the first chamber inlet 103 such that the reagents, such as the sample and the coated beads, may be loaded into the first chamber 101. In some examples, the coated beads may be pre-loaded into the first chamber 101, for example the beads may be loaded during manufacturing of the assay device 100. In this manner, the assay device 100 may not require a user to load the beads, thereby increasing the ease of use of the assay device 100. In some examples, the first chamber 101 may be positioned adjacent to a first portion 901 of the second chamber 102. The control region 105 may be located anywhere that the first chamber 101 and the second chamber 102 are adjacent to one another. In some examples, the control region 105 may be located at a peripheral region of the first chamber 101 that overlaps with a peripheral region of the first portion 901 of the second chamber 102.

The first chamber layer 201 may be separated from the second chamber layer 202 by a control layer 204. The control layer 204 may be formed from a number of materials, such as a wax, a polymer, a photoresponsive material, a chemoresponsive material, glass, thermoplastics, or combinations thereof. The control layer 204 may open at the control region 105 by, for example, being punctured or by deforming in response to being exposed to a material or a stimulus. A control layer 204 formed from a wax, for example paraffin, may open responsive to a heat stimulus, which may cause the wax to melt, thereby providing a fluid connection between the first chamber 101 and the second chamber 102. As wax is typically less dense than water, the molten wax may float on top of the aqueous layer and not interfere with the assay. A control layer 204 formed from a polymer may open responsive to heating with an infrared LED, which may cause the polymer to burn away, thereby providing a fluid connection between the first chamber 101 and the second chamber 102. A control layer 204 formed from a photoresponsive material may open responsive to exposure to UV light to provide a fluid connection between the first chamber 101 and the second chamber 102. In some examples, the photoresponsive material may transform from a gel to a liquid responsive to the UV light. A control layer 204 formed from a chemoresponsive material may open responsive to a change in pH, which may cause some materials to melt away and provide a fluid connection between the first chamber 101 and the second chamber 102. A control layer 204 formed from a thermoplastic material, for example an acetate, acrylate, polyethylene derivative, or combinations thereof, may open responsive to a heat stimulus, which may cause the thermoplastic to melt, thereby providing a fluidic connection between the first chamber 101 and the second chamber 102.

The control layer 204 may have a thickness in the range of 2 µm to 500 µm, for example 150 µm. In some examples, the control layer 204 may be between 100-500 µm thick, in some examples 2-100 µm thick, in some examples 100-200 µm thick, in some examples 200-300 µm thick, in some examples 300-400 µm thick, in some examples 400-500 µm thick, in some examples 2-250 µm thick, and in some examples 250-500 µm thick. It may be desirable to form the control layer 204 to be thick enough such that it does not open on its own, but not so thick that it is difficult to open. In some examples, a dye or an energy-absorbing agent may be included in the control layer 204 to make it more sensitized to the stimulus being used to open it. For example, when using an infrared LED to open a control layer 204 formed from a polymer, an infrared absorbing dye may be incorporated into the control layer 204. Exposure to infrared light may cause the infrared absorbing dye to rise in temperature, thereby facilitating opening of the control layer 204. Similarly, a heat-sensitive dye may be incorporated into the control layer 204 when using a heat stimulus in order to facilitate opening of the control layer 204. In some examples, the temperature may rise to a melting point of the control layer 204.

The control layer 204 may include a second vent passage 208 that may be coupled to the first vent passage 207 to provide a conduit whereby air may pass through such that pressure gradients across the multiple layers of the assay device 100 may be reduced. The control layer 204 may include a second second chamber passage 206 that may be coupled to the first second chamber passage 205 to provide a conduit for reagents to be loaded into the second chamber 102. In some examples, multiple control layers may be provided to provide fluidic connections between different sets of layers of the assay device 100.

The second chamber layer 202 of the assay device 100 may include a second chamber 102 coupled to one or more of the second second chamber passage 206, the control region 105, and the second vent passage 208. The second chamber layer 202 may be positioned adjacent to the control layer 204. The second chamber 102 may be loaded with reagents through the conduit created by the second chamber inlet 104, the first second chamber passage 205 and the second second chamber passage 206. The second chamber 102 may be vented by the conduit provided by the vent 106, the first vent passage 207, and the second vent passage 208.

The second chamber 102 may be a compartment, recess, or another type of structure shaped to house a density media, a labeling agent, or combinations thereof. The second chamber 102 may be coupled to the second chamber inlet 104, the first second chamber passage 205 and the second second chamber passage 206 such that the reagents, such as the density media and the labeling agent, may be loaded into the second chamber 102. In some examples, the density media and the labeling agent may be pre-loaded into the second chamber 102. For example the density media and the labeling may be loaded during manufacturing of the assay device 100. In this manner, the assay device 100 may not require a user to load the density media or the labeling agent, thereby increasing the ease of use of the assay device 100. The second chamber 102 may include a first portion 901, a second portion 900, and a detection region 902. In some examples, the first portion of the second chamber 102 may be positioned adjacent to the first chamber 101. The control region 105 may be positioned anywhere that the first chamber 101 and the second chamber 102 are adjacent to one another. In some examples, the control region 105 may be located at a peripheral region of the first chamber 101 that overlaps with a peripheral region of the first portion 901 of the second chamber 102.

Figure 3:
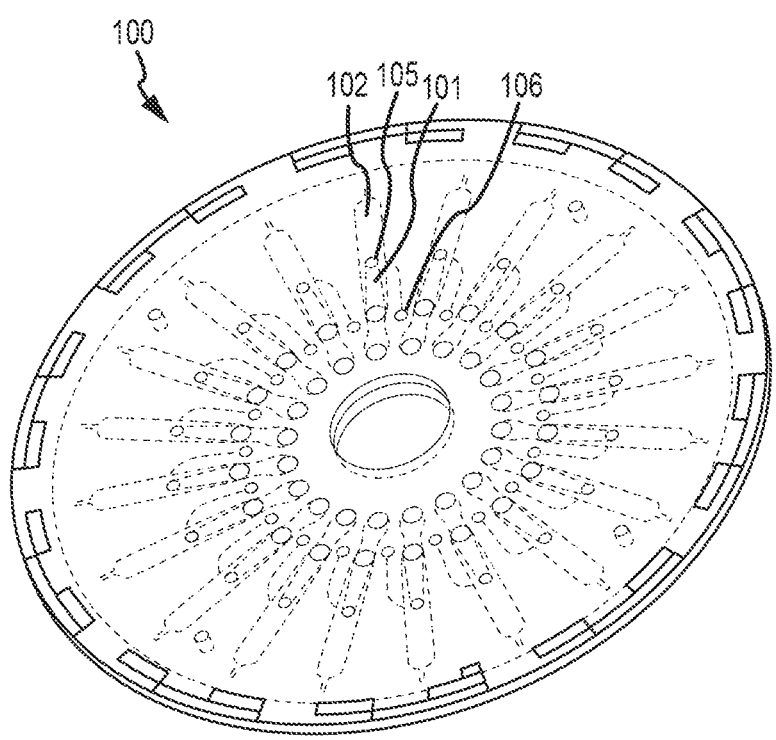
FIG. 3 is a bottom up schematic illustration of an assay device arranged in accordance with examples of the present invention.

FIG. 3 is a bottom up schematic illustration of an assay device 100, according to some embodiments. The assay device 100 may be generally flat on a bottom side. In some examples, the assay device 100 may include features on the bottom side for optical encoding. The features may include patterns that may be used as a rotary encoder rather than having an encoder on the motor 108. The features may be tracked using an optical transceiver that may relay positional information to the controller 1004. The features may be formed by known manufacturing methods including, but not limited to, microfluidic manufacturing techniques and semi-conductor manufacturing techniques. Techniques such as injection molding, etching, cutting, or combinations thereof, may be used. In some examples, etching may be used on the surface of the bottom layer 203 to create reflective and diffuse areas that may enable optical encoding.

Figure 4:
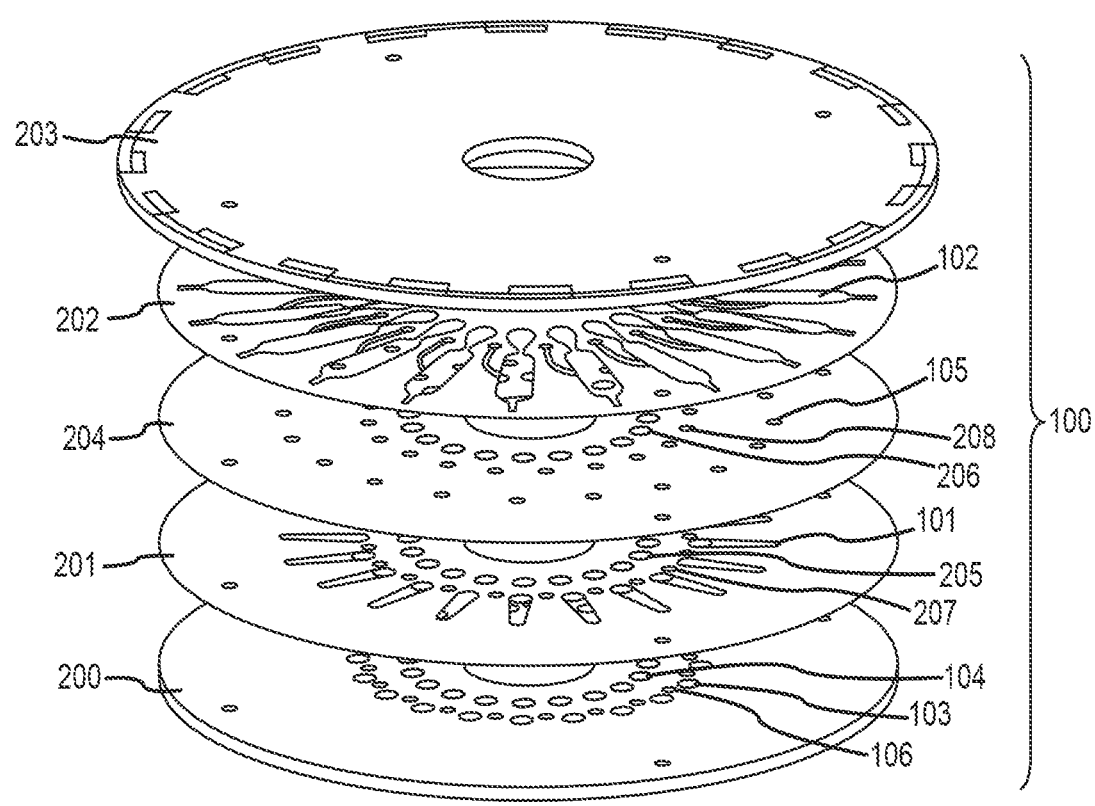
FIG. 4 is a bottom up exploded schematic illustration of an assay device arranged in accordance with examples of the present invention.

FIG. 4 is a bottom up exploded schematic illustration of an assay device, according to some embodiments. The bottom layer 203 of the assay device 100 may be a substrate formed by techniques such as injection molding, cutting, or both. The bottom layer 203 may provide a base for the assay device 100. In some examples, the bottom layer may be positioned adjacent to the second chamber layer 202.

Figure 5:
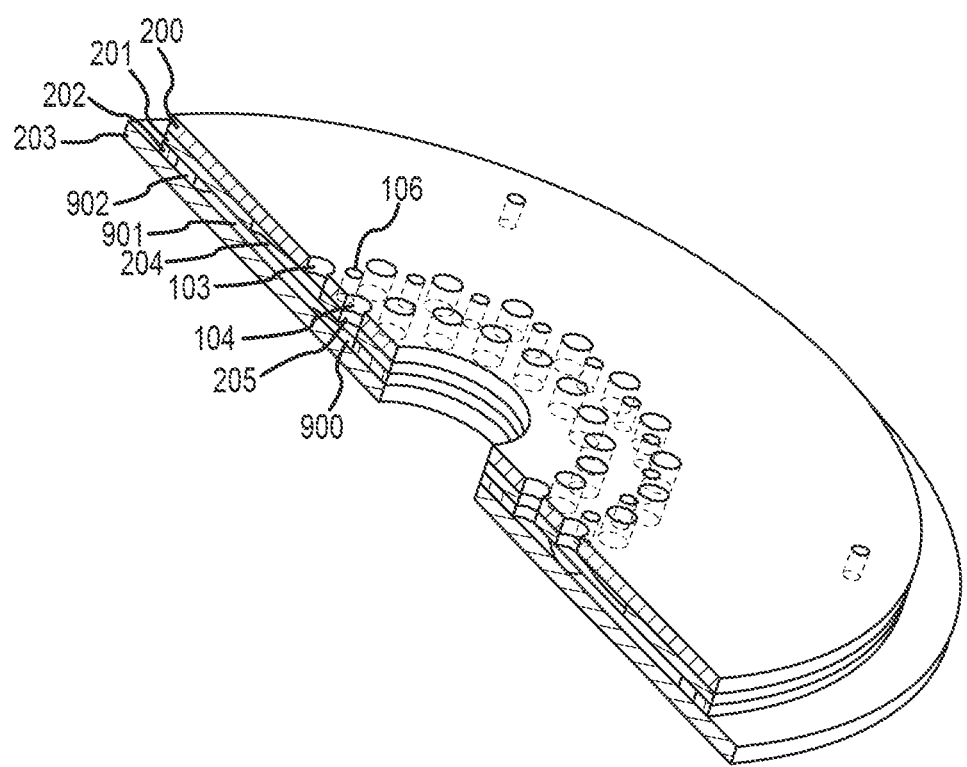
FIG. 5 is a cross-sectional schematic illustration of an assay device according to examples of the present invention.

FIG. 5 is a cross-sectional schematic illustration of an assay device 100, according to some embodiments. As shown in the cross-sectional portion of FIG. 5, the first chamber inlet 103 may be a conduit that passes through the inlet layer 200 and into the first chamber 101. The bottom of the first chamber 101 may be provided by the control layer 204. The second chamber inlet 104 may be a conduit that passes through the inlet layer 200, the first chamber layer 201 and the control layer 204 where it may reach the second chamber 102. FIG. 5 shows an example where the second chamber 102 extends further to the periphery of the assay device 100 compared to the first chamber 101. In some examples, the peripheral end of the second chamber 102 may include a detection region 902, as will be described below.

Figure 6:
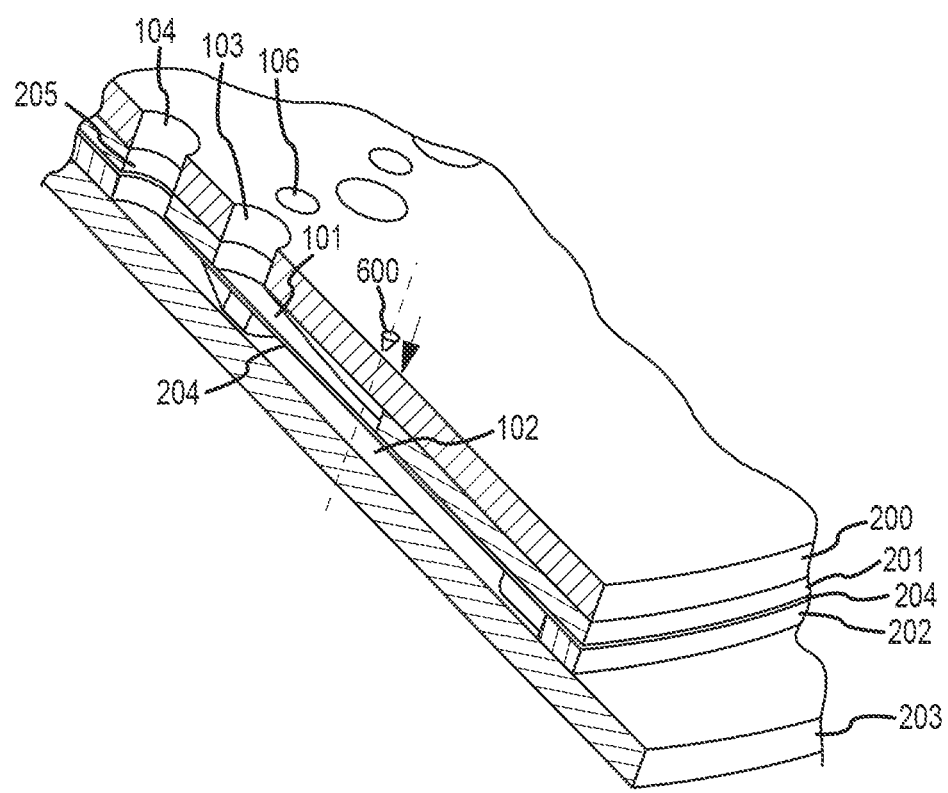
FIG. 6 is a cross-sectional schematic illustration of an assay device prior to opening a control layer in accordance with examples of the present invention.

FIG. 6 is a cross-sectional schematic illustration of an assay device 100 prior to opening a control layer 204, according to some embodiments. Prior to opening the control layer 204, the first chamber 101 may be fluidly disconnected from the second chamber 102. A pin 600 may be placed within or proximate to the assay device 100, as will be described below. The first chamber may be sized such that the contents of the first chamber 101 may be in the laminar flow regime prior to opening the control layer 204. While in the laminar flow regime, the contents of the first chamber 101 may not mix with each other, even during a time when the device may be spinning to apply centrifugal force to the fluids contained therein. The second chamber 102 may also be sized such that the contents of the second chamber 102 may be in the laminar flow regime prior to opening the control layer 204. While in the laminar flow regime, the contents of the second chamber 101 may not mix with each other, even during a time when the device may be spinning to apply centrifugal force to the fluids contained therein.

Figure 7:
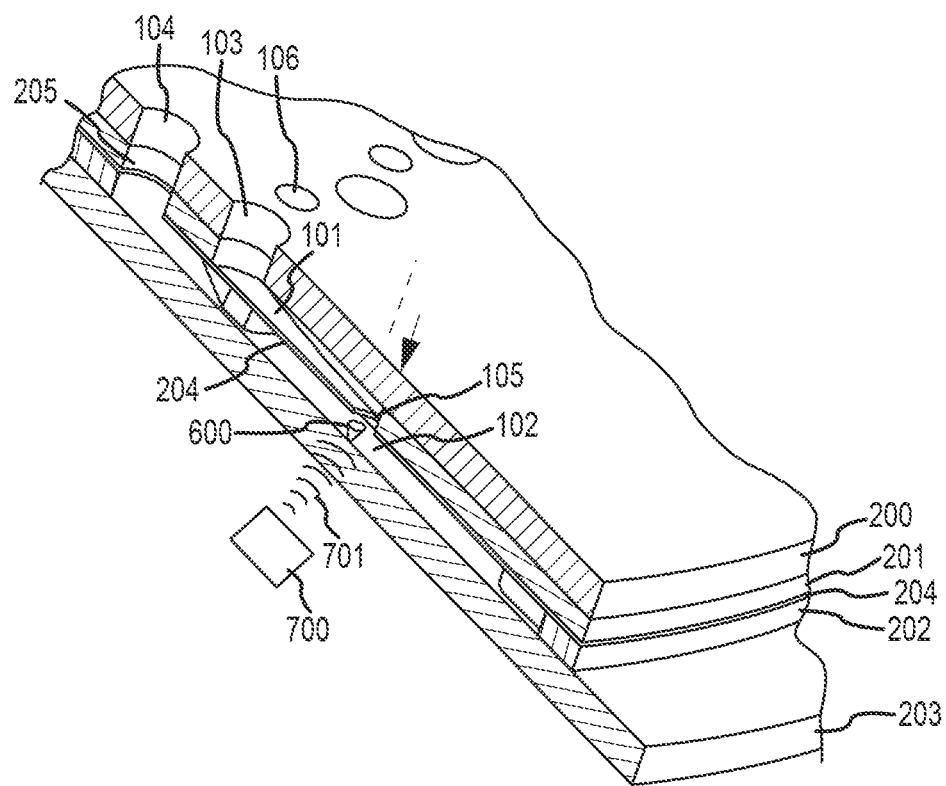
FIG. 7 is a cross-sectional schematic illustration of an assay device after opening a control layer in accordance with examples of the present invention.

FIG. 7 is a cross-sectional schematic illustration of an assay device after opening a control layer, according to some embodiments. In some examples, the assay device 100 may include multiple assay sets, each of which includes a first chamber 101 and a second chamber 102. In some examples, one or more pins 600 may be used to open the control layer 204 at one or more control regions 105 of the assay device 100, thereby achieving a fluidic connection of the chambers of each assay set. In some examples, the pins 600 may be positioned adjacent to the control regions 105 of the control layer 204 such that they may be moved through the control regions 105 responsive to a force or stimulus. In some examples, the pins 600 may be incorporated into one of the layers, for example the inlet layer 200 or the first chamber layer 201. In some examples, the pins 600 may be formed of metal, and may be moved by applying a magnetic field 701 across the assay device 100 by a magnet 700, for example an electromagnet. The magnetic field 701 may apply a force to the pins 600 such that the pins 600 travel through the control regions 105 and create an opening to provide a fluid connection between each first chamber 101 and each first portion 901 of the second chamber 102. In some examples, an actuator may apply a mechanical force to move the pins 600 through the control regions 105 to provide a fluidic connection between each first chamber 101 and each first portion 901 of the second chamber 102. In some examples, multiple pins 600 may be moved simultaneously to open multiple control regions 105.

FIG. 7 shows an example where the control region 105 may be at the peripheral end of the first chamber 101. However, it will be understood that the control region 105 may be positioned at any region in which the first chamber 101 and the first portion 901 of the second chamber 102 are adjacent to one another. Furthermore, the control region 105 may vary in size. For example, when the entire first chamber 101 is adjacent to the first portion 901 of the second chamber 102, the control region 105 may include the entire first chamber 101. In this example, the control layer 204 may be opened to fully connect the first chamber 101 with the first portion 901 of the second chamber 102. Thus, the control layer 204 may be at least partially opened to provide a fluid connection between the first chamber 101 and the first portion 901 of the second chamber 102. In some examples, there may be multiple control regions that may be opened to provide fluidic connections between two or more chambers. The multiple control regions may be positioned on the same control layer or on multiple control layers.

In some examples, the control layer 204 may be opened in response to a stimulus, such as UV light, infrared light, or a pH change. It may be advantageous to use a stimulus when the control region 105 is an irregular shape or to ensure that the pins do not obstruct pathways in the second chamber 102. UV light or infrared light may be applied by known methods across the assay device 100, whereby the light travels through the layers of the assay device 100 until it reaches the control layer 204. The control layer 204, which may be formed from a photoresponsive material, may open in response to exposure to the UV light or infrared light, thereby providing a fluid connection between the first chamber 101 and the first portion 901 of the second chamber 102. A pH change may be initiated by introducing a base or an acid through the first chamber inlet 101. The base or acid may change the pH of the contents of the first chamber 101, causing the control layer 204 to open, thereby providing a fluid connection between the first chamber 101 and the first portion 901 of the second chamber 102.

Upon opening the control layer 204, the contents of the first chamber 101 and the first portion 901 of the second chamber 102 may mix together. The device may be agitated and/or spun to facilitate the mixing. The increase in the channel (or chamber) height from combining the first chamber 101 and the first portion 901 of the second chamber 102 by opening or deforming the control layer may result in the overall combined fluidic feature moving from the laminar flow regime to a turbulent flow regime. Accordingly, the contents of the first chamber 101 and the first portion 901 of the second chamber 102 may mix responsive to the turbulent flow in the first portion of the second chamber, which may be generated by moving and/or agitating the device 100, for example. In some examples, the assay device 100 may be moved to achieve mixing. A motor or manual force may be used to move the assay device 100. The channel height of the second portion 900 of the second chamber 102 may remain constant after opening the control layer 204. Thus, the contents of the second portion 900 may stay in the laminar flow regime. Therefore, the mixing may occur in the first portion 901 of the second chamber 102 without mixing contents of the second portion 900 of the second chamber 102.

Figure 8:
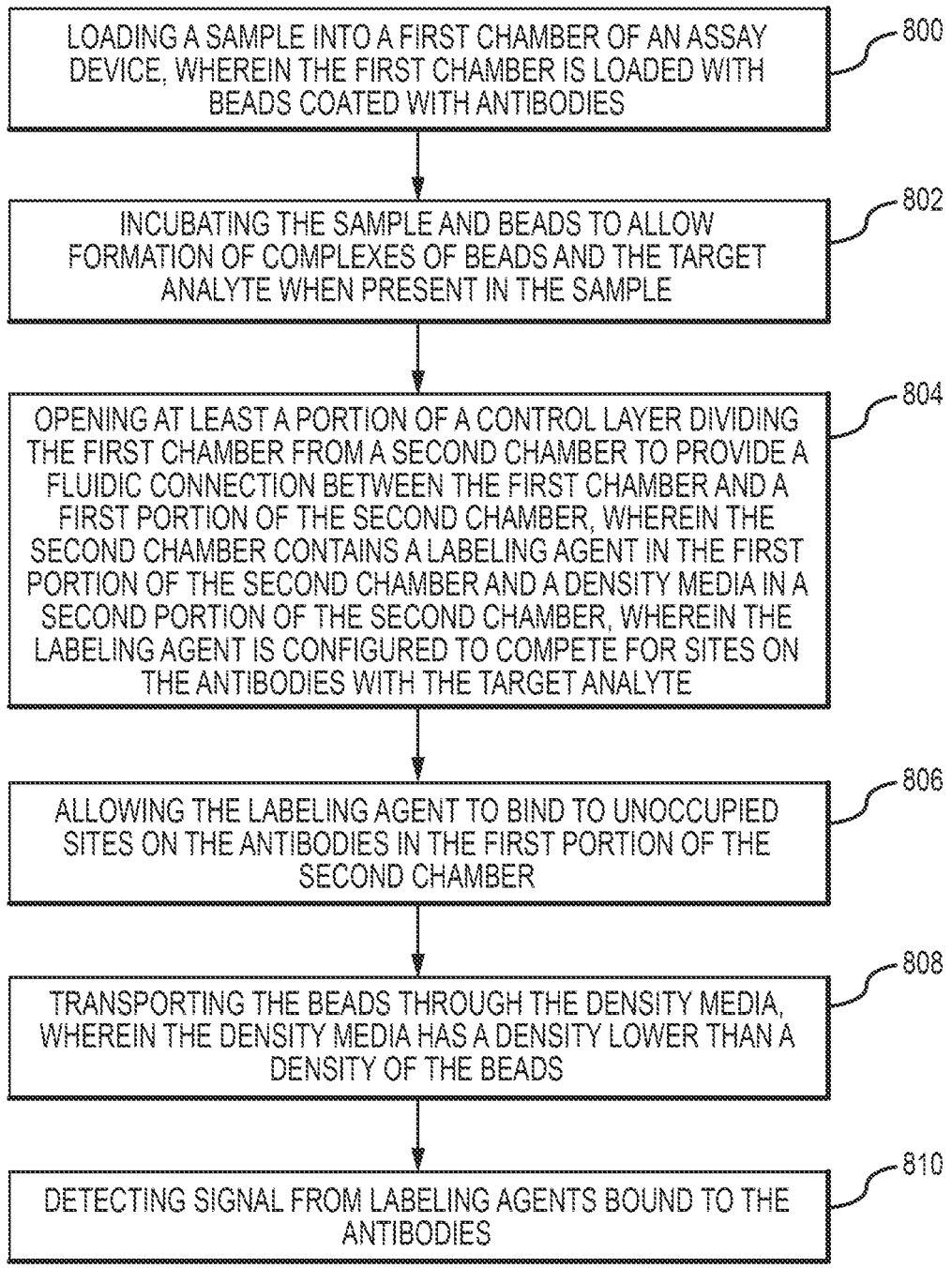
FIG. 8 is a flowchart depicting a method for performing an assay, according to examples of the present invention.

FIG. 8 is a flowchart depicting a method for performing an assay, according to embodiments described herein. Operation 800 involves loading a sample into a first chamber (e.g. 101 of FIG. 2) of an assay device, wherein the first chamber is loaded with beads coated with antibodies. Operation 802 involves incubating the sample and beads to allow formation of complexes of beads and the target analyte when present in the sample. In some examples, the incubation time may be in the range of about 0.5 minutes to about 6 hours. Operation 804 involves opening at least a portion of a control layer (e.g. 204 of FIG. 2) dividing the first chamber from a second chamber (e.g. 102 of FIG. 2) to provide a fluidic connection between the first chamber and a first portion (e.g. 901 of FIG. 9) of the second chamber, wherein the second chamber contains a labeling agent in the first portion of the second chamber and a density media in a second portion (e.g. 900 of FIG. 9) of the second chamber, wherein the labeling agent is configured to compete for sites on the antibodies with the target analyte. In some examples, the second chamber may be vented after opening at least a portion of the control layer through a vent (e.g. 106 of FIG. 1) coupled to the second chamber. In some examples, the beads may be transported from the first chamber to the second chamber by a pressure gradient after providing the fluidic connection. In some examples, the plurality of beads and the labeling agent may be mixed after opening at least a portion of the control layer. Operation 806 involves allowing the labeling agent to bind to unoccupied sites on the antibodies in the first portion of the second chamber. Operation 808 involves transporting the beads through the density media, wherein the density media has a density lower than a density of the beads.

Operation 810 involves detecting signal from labeling agents bound to the antibodies. The measurement may be performed using the detection unit. In some examples, the measurement may be performed during the predetermined interval where the assay device 100 is stopped, for example by stopping a stepper motor or engaging a stopping mechanism. For example, the measurement may detect fluorescence present in the detection region, which may allow identification of analyte including, but not limited to biomolecules such as proteins, nucleic acids, or combinations thereof. The method of FIG. 8 may be implemented using any of the structures shown in FIGS. 1-7 and FIGS. 9-10 in some examples.

Figure 9:
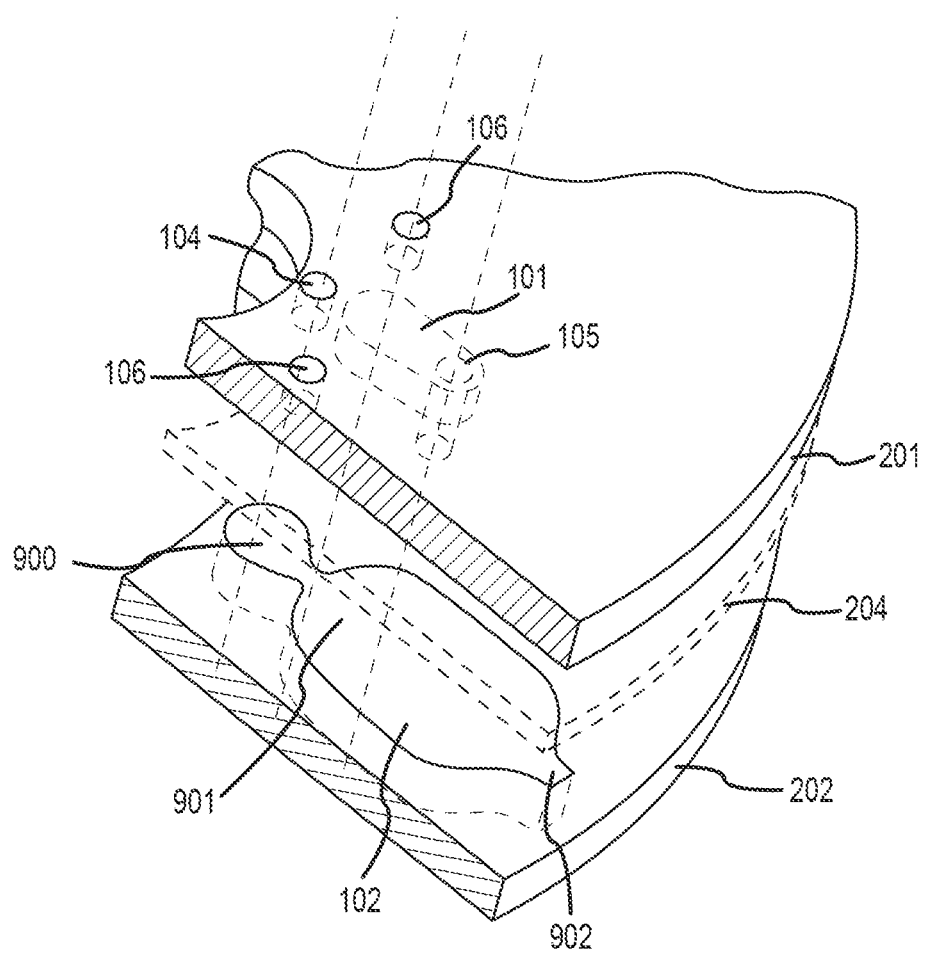
FIG. 9 is a top down exploded schematic illustration of the first chamber layer, the control layer, and the second chamber layer in accordance with examples of the present invention.

FIG. 9 is a top down exploded schematic illustration of the first chamber layer 201, the control layer 204, and the second chamber layer 202, according to some embodiments. The first portion 901 of the second chamber 102 may contain a first reagent, for example the labeling agent. The labeling agent may be any suitable labeling agent for binding to the antibodies and providing a detection signal. Examples include chemical dyes and/or nucleic acid dyes. Fluorescent labels including the aforementioned chemical dyes may provide an optical detection signal, however colorimetric or radioactive tags may also be used. The first portion 901 may be a compartment, recess, or another type of structure. The first portion 901 may be coupled to the second portion 900 of the second chamber 102. Prior to opening the control layer 204, the first portion 901 may be sized for laminar flow. While in the laminar flow regime, the first reagent may be substantially static such that little mixing occurs between the first reagent and a second reagent in the second portion 900. In some examples, the end of the first portion 901 closest to the second portion 900 may be relatively narrow so as to further inhibit mixing between the first reagent and the second reagent.

The second portion 900 of the second chamber 102 may contain the second reagent, for example the density media. The second portion 900 may be a compartment, recess, or another type of structure. The second portion 900 may be coupled to the first portion 901. The second portion 900 may be sized for laminar flow. While in the laminar flow regime, the second reagent may be substantially static such that little mixing occurs between the first reagent and the second reagent. In some examples, the end of the second portion 900 closest to the first portion 901 may be relatively narrow so as to further inhibit mixing between the first reagent and the second reagent. In some examples, the second portion 900 of the second chamber 102 may stay in the laminar flow regime after a fluidic connection is established between the first chamber 101 and the first portion 901 of the second chamber 102. Thus, the density media loaded in the second portion 900 may not mix with the complexes formed between the coated antibodies, target antigen, and the labeling agent until a centrifugal force is applied, as will be described below.

The density media may have a density greater than the sample, but less than that of the beads. For example, a blood sample may have a density less than or equal to 1.095 g/cm$^3$, and beads formed from silica may have a density of about 2.05 g/cm$^3$. Accordingly, the density may have a density of between 1.095 g/cm$^3$ and 2.05 g/cm$^3$. In some examples, the density media may have a density of 1.11 g/cm$^3$. The density media may include, for example, a salt solution containing a suspension of silica particles which may be coated with a biocompatible coating. An example of a suitable density media is Percoll™, available from GE Lifesciences.

A detection region 902 may be positioned along a known path to align with a detection unit 1002. In some examples, the known path may be defined by a radius from the center of a circular assay device 100. In some examples, the detection region 902 may be coupled to the first portion 901 of the second chamber 102. The detection region 902 may be a compartment, recess or another type of structure shaped to concentrate a component to be detected by the detection unit 1002. In some examples, the detection region 902 may be shaped to accommodate beads that may get pelleted through the density media responsive to a centrifugal force applied by a motor, as will be described below.

Figure 10:
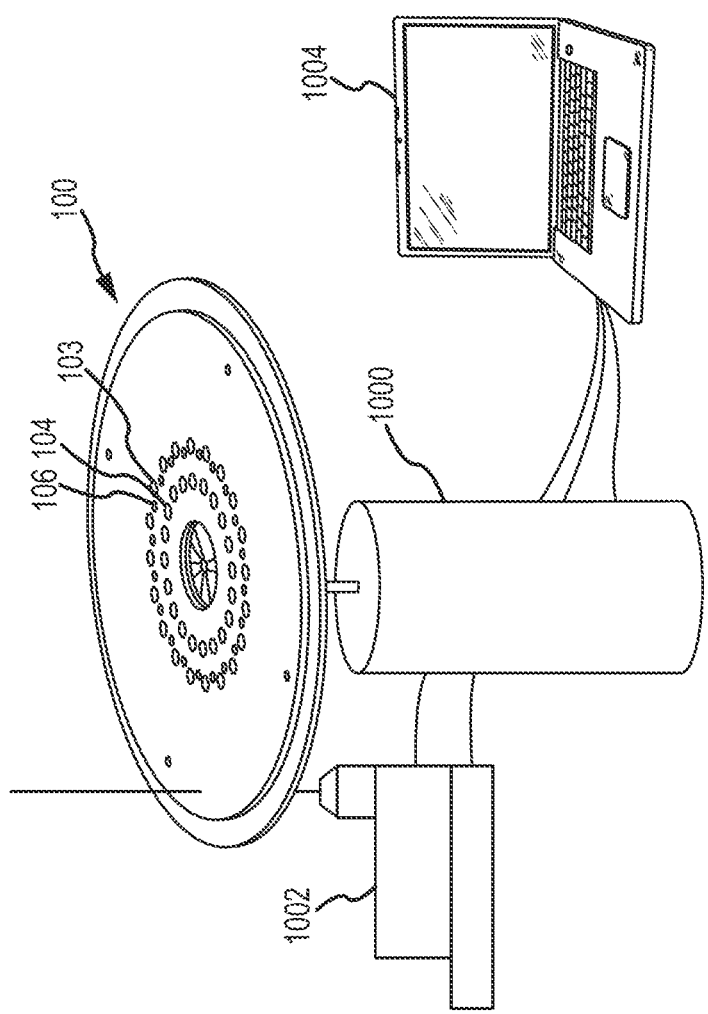
FIG. 10 is a schematic illustration of a system for conducting an assay in accordance with examples of the present invention.

FIG. 10 is a schematic illustration of a system for conducting an assay, according to some embodiments. The system may include the assay device 100, a motor 1000, a detection unit 1002, and a controller 1004. The motor 1000 may move the assay device 100 such that multiple detection regions may move along a known path. In some examples, the path may be circular. In some examples, the path may be linear. The motor 1000 may be a DC motor coupled to the assay platform 100, such as a stepper motor. In some examples, other types of motors, such as solenoid motors, servo motors, or combinations thereof may be used in conjunction with a stopping mechanism. The stopping mechanism may allow the assay device 100 to be moved in a known manner such that the detection regions 902 present on the assay device 100 may sequentially align with the detection unit 1002.

In some examples, the motor 1000 may apply a centrifugal force to an assay device 100 mounted in the system. Centrifugal force may be used to separate one or more components of one or more samples positioned within the connected first chamber and second chamber of the assay platform 100. For example, components of biological and clinical samples may need to be separated to facilitate measurement (e.g. detection and/or quantification) of an analyte. Applying a centrifugal force may achieve a separation of one or more components of the biological or clinical samples placed within one or more of the connected first chambers and second chambers of the assay platform 100. In some examples, a fluid sample positioned within one or more of the connected first chambers and second chambers may include a plurality of beads having complexes formed thereon, in which individual ones of the complexes include a target analyte and a labeling agent bound to the beads in cooperation with the target analyte. The fluid sample may also include free labeling agent that may be unbound. The motor 1000 may apply a centrifugal force to the fluid sample, whereby the beads in the fluid sample may be transported responsive to the centrifugal force through a density media to pellet out at the detection region 902. Free labeling agent may have insufficient density to be transported through the density media and may not be present at the detection region 902. It should be understood that the motor 1000 may be configured to move the assay device 100 to effect a separation of a variety of different types of assays responsive to a centrifugal force. Examples of assays usable with examples of the present invention are described in the applications incorporated by reference above.

The detection unit 1002 may perform measurements to detect and/or quantify an analyte in any or all of the detection regions 902 present on the assay device 100. The detection unit 1002 may, for example, include an optical light sensor for performing optical measurements, such as fluorescence, luminescence, and/or relative light absorption. In some examples, other sensors (e.g. electrical sensors) may be included additionally or instead in the detection unit 1002 to support other detection methodologies. The detection unit 1002 may be mounted in a system in proximity to a mount for holding the assay device 100. Generally, the detection unit 1002 is positioned in a system such that a detection region 902 is aligned with the detection unit 1002 such that detection unit 1002 is positioned to take a measurement from the detection region 902, or to move in a known manner to the detection region 902. A mount may be provided in a system for receiving the assay device 100 which may generally be inserted into and removed from the system. The detection unit 1002 may accordingly be positioned in a known manner relative to the mount to facilitate alignment between detection regions on devices that may be placed on the mount and the detection unit 1002.

In some examples, the controller 1004 may be communicatively coupled (e.g. electrically) to the motor 1000. The controller 1004 may be an electronic device, for example a computing device, that may transmit control signals at predefined times and/or predefined intervals to recipient devices. Additionally, the controller 1004 may store timing information using a timing device, for example a timer integrated circuit. The control signals may be transmitted using an implementation of a protocol recognizable by the recipient devices. The recipient device may include the detection unit 1002 and/or the motor 1000. The controller 1004 may receive user input that defines parameters of the measurement system, such as distance between each of the detection regions 902, rotational speed, etc. The controller 1004 may provide control signals to the motor 1000 to sequentially measure each detection region 902 of the assay device 100. In some examples, the controller may communicate with an optical transceiver to receive positional information. In some examples, the controller 1004 may stop the motor 1000 for a predetermined period of time at each detection region 902 to make a measurement. It may be advantageous to take a measurement while the assay device 100 is not moving in order to increase the integration time for light (or other signal) collection, which may increase the signal to noise ratio and hence sensitivity. It may be advantageous to stop the motor 1000 for a predetermined period of time to reduce electrical noise originating from the active motor during analysis by the detection unit 1002. After a predetermined time, the controller 1004 may again provide control signals to start the motor 1000 to move the assay device 100 such that the next detection region 902 may be in alignment with the detection unit 1002.

In some examples, the controller 1004 may receive an indication that a sample was received in the first chamber 101. The indication may be provided by a sensor positioned inside or proximate to the first chamber 101. After receiving the indication, the controller 1004 may allow an incubation period to take place, after which it may provide a control signal to open at least a portion of the control layer 204. In some examples, the control signal may be provided to an actuator, which may apply a mechanical force to create an opening in the control layer 204. For example, the mechanical force may be applied to one or more pins, whereby the pins 600 puncture the control layer 204 to provide a fluidic connection between the first chamber 101 and the first portion 901 of the second chamber 102. In some examples, the control signal may be provided to a magnet 700 to provide a magnetic force 701 to move metal pins 600 through the control layer 204. In some examples, the control signal 204 may be provided to known devices to deliver ultraviolet light, infrared light, an acid or base, or combinations thereof.

In some examples, the controller 1004 may provide a control signal to the motor 1000 to move the assay device 100 to achieve mixing. Mixing may be desired at a number of stages of a competition assay. In some examples, mixing may be desired after loading the sample into the first chamber 101 in order to facilitate binding of the sample to the antibodies in the first chamber 101. As described above, the antibodies may coated on to beads. In some examples, mixing may be desired after providing a fluidic connection between the first chamber 101 and the first portion 901 of the second chamber 102 in order to facilitate binding of the labeling agent to unoccupied sites on the antibodies. In some examples, the motor 1000 may rotate the assay device 100 back and forth to achieve mixing in the first portion 901 of the second chamber 102.

In some examples, the controller 1004 may provide a control signal to the motor 1000 to move the assay device 100 to apply a centrifugal force. A centrifugal force may be achieved by spinning the assay device 100 using the motor 1000. As described above, the centrifugal force may be used to separate the contents of one or more assay sets of the assay device 100. In some examples, beads may be transported through the density media in response to the centrifugal force applied by the motor 1000. The beads may be transported to the detection region 902 for measurement by the detection unit 1002.

The assay device 100 may be used to perform a variety of tasks involving staged delivery and management of fluids. In some examples, the assay device 100 may be used to conduct a bead-based nucleic acid assay, such as a PCR assay or a hybridization-based assay. The nucleic acid assay may utilize any of molecular beacons and Taqman chemistry. In addition, the assay device may be used to conduct immunoassays, such as a sandwich assay. Further, the assay device 100 may be used to conduct an affinity assay using aptamers, peptides, PNAs, SCFVs, or combinations thereof. In addition, the assay device 100 may be used to conduct an assay utilizing enzymatic activity. The enzymatic activity may provide an amplification of the detection signal. Further, the assay device 100 may be used to perform sample preparation. The sample preparation technique may include a buffer exchange, for example transferring beads from a clinical or environmental sample to an assay buffer. In some examples, the buffer exchange may change the pH or the ionic strength of the sample. In some examples, the buffer exchange may stabilize the sample by using a second buffer including stabilization reagents. The stabilized sample may be archived and retrieved from the assay device 100.

From the foregoing it will be appreciated that, although specific embodiments of the invention have been described herein for purposes of illustration, various modifications may be made without deviating from the spirit and scope of the invention.

What is claimed is:

1. An assay device comprising:
   a first chamber layer comprising a first chamber containing a plurality of beads and configured to receive a sample;
   a second chamber layer comprising a second chamber proximate the first chamber, the second chamber comprising a first portion positioned adjacent to the first chamber and a second portion, wherein the second portion contains a density media; and
   a control layer positioned between the first chamber layer and the second chamber layer, wherein the control layer comprises a control region configured to be at least partially opened to provide a fluidic connection between the first chamber and the first portion of the second chamber.

2. The assay device of claim 1, wherein the control layer is formed from a wax, a polymer, a photoresponsive material, a chemoresponsive material, a glass, a thermoplastic, or a combination thereof.

3. The assay device of claim 1, further comprising one or more pins positioned adjacent to the control region, wherein the one or pins are configured to create an opening at the control region in the control layer.

4. The assay device of claim 3, wherein the first chamber and the second chamber comprise a first assay set, and wherein the assay device further comprises multiple assay sets.

5. The assay device of claim 4, further comprising multiple pins corresponding to each assay set, wherein the multiple pins are positioned to create multiple openings in the control layer.

6. The assay device of claim 3, wherein the one or more pins are configured to create an opening at the control region in the control layer responsive to a magnetic force.

7. The assay device of claim 3, wherein the assay device comprises one or more recesses in the second chamber configured to house the one or more pins.

8. The assay device of claim 1, further comprising one or more additional chambers or one or more additional control layers.

9. The assay device of claim 8, wherein at least one of the one or more additional chambers are separated from the first chamber or from the second chamber by the control layer or by one of the one or more additional control layers.

10. The assay device of claim 8, further comprising at least two additional chambers, wherein at least one of the one or more additional control layers are positioned between the at least two additional chambers to provide fluidic connection the at least two additional chambers.

11. The assay device of claim 1, wherein the control region comprises a pin, a wax, a photoresponsive material, a chemoresponsive material, or a thermoplastic.

12. The assay device of claim 1, wherein the first portion contains a labeling agent.

13. The assay device of claim 12, wherein the labeling agent comprises a labeled antigen.

14. The assay device of claim 1, wherein the first chamber layer comprises a plurality of first chambers, wherein the second chamber layer comprises a plurality of second chambers, and wherein the control layer comprises a plurality of control regions, in which each control region is configured to be at least partially opened to provide a fluidic connection between one of the plurality of first chamber and one of the plurality of second chambers.

15. A system for conducting an assay comprising:
   an assay device comprising a first chamber layer comprising a first chamber and a second chamber layer comprising a second chamber, wherein the first chamber contains a plurality of beads, wherein the second chamber comprises a first portion and contains a density media in a second portion and comprises a detection region, wherein the first portion is positioned adjacent to the first chamber, and wherein the first chamber layer and the second chamber layer are separated by a control layer comprising a control region configured to be at least partially opened to provide a fluidic connection between the first chamber and the first portion of the second chamber;
   a motor coupled to the assay device, the motor configured to move the assay device; and
   a detection unit positioned proximate to the assay device, the detection unit configured to detect a signal from the detection region.

16. The system of claim 15, further comprising a controller, wherein the controller is configured to:
   receive an indication sample was received in the first chamber;
   after an incubation time, provide a control signal to an actuator to open the control region of the control layer; and
   move the assay device to transport the plurality of beads through the density media.

17. The system of claim 16, wherein the controller is configured to spin the assay device to apply a centrifugal force to transport the plurality of beads through the density media.

18. The system of claim 15, wherein the control layer is formed from a wax, a polymer, a photoresponsive material, a chemoresponsive material, a glass, a thermoplastic, or a combination thereof.

19. The system of claim 15, wherein the assay device comprises at least one pin positioned adjacent to the control region, and wherein the controller is configured to create an opening at the control region by positioning a magnet to pull the at least one pin through the control layer.

20. The system of claim 15, wherein the first chamber and the second chamber comprise a first assay set, and wherein the assay device further comprises multiple assay sets.

21. The system of claim 15, wherein the controller is configured to achieve mixing in the first portion of the second chamber.

22. The system of claim 21, wherein the mixing occurs in the first portion of the second chamber through turbulent flow without mixing contents of the second portion of the second chamber.

23. The system of claim 22, wherein the second portion of the second chamber is sized for laminar flow.

24. The system of claim 21, wherein the controller is configured to rotate the assay device back and forth to achieve mixing in the first portion of the second chamber.

25. The system of claim 15, wherein the control region comprises a pin, a wax, a photoresponsive material, a chemoresponsive material, or a thermoplastic.

26. The system of claim 25, further comprising:
   a heat stimulus, a light, or a magnet configured to be applied to the control region.

27. The system of claim 15, wherein the first portion contains a labeling agent.

28. The system of claim 27, wherein the labeling agent comprises a labeled antigen.

29. The system of claim 15, wherein the first chamber layer comprises a plurality of first chambers, wherein the second chamber layer comprises a plurality of second chambers, and wherein the control layer comprises a plurality of control regions, in which each control region is configured to be at least partially opened to provide a fluidic connection between one of the plurality of first chamber and one of the plurality of second chambers.

30. An assay device comprising:
- a first chamber containing a plurality of beads and configured to receive a sample;
- a second chamber proximate the first chamber, the second chamber comprising a first portion positioned adjacent to the first chamber and a second portion, wherein the second portion contains a density media;
- a control layer positioned between the first chamber and the second chamber, wherein the control layer comprises a control region configured to be at least partially opened to provide a fluidic connection between the first chamber and the first portion of the second chamber; and
- one or more pins positioned adjacent to the control region, wherein the one or pins are configured to create an opening at the control region in the control layer.

31. The assay device of claim 30, wherein the first chamber and the second chamber comprise a first assay set, and wherein the assay device further comprises multiple assay sets.

32. The assay device of claim 31, further comprising multiple pins corresponding to each assay set, wherein the multiple pins are positioned to create multiple openings in the control layer.

33. The assay device of claim 30, wherein the one or more pins are configured to create an opening at the control region in the control layer responsive to a magnetic force.

34. The assay device of claim 30, wherein the assay device comprises one or more recesses in the second chamber configured to house the one or more pins.

* * * * *